United States Patent [19]

Capet et al.

[11] Patent Number: 5,624,939
[45] Date of Patent: Apr. 29, 1997

[54] N-ACYL PYRROLIDINES AND DRUGS FOR THE TREATMENT OR PREVENTION OF CHOLECYSTOKININ AND GASTRIN-RELATED DISORDERS

[75] Inventors: Marc Capet, Thiais; Marie-Christine Dubroeucq, Enghein les Bains, both of France

[73] Assignee: Rhone-Poulenc Rorer, S.A., Antony, France

[21] Appl. No.: 448,406

[22] PCT Filed: Jan. 3, 1994

[86] PCT No.: PCT/FR94/00008

§ 371 Date: Jun. 28, 1995

§ 102(e) Date: Jun. 28, 1995

[87] PCT Pub. No.: WO94/15914

PCT Pub. Date: Jul. 21, 1994

[30] Foreign Application Priority Data

Jan. 7, 1993 [FR] France ................... 93 00077

[51] Int. Cl.⁶ .................. A61K 31/40; C07D 207/16
[52] U.S. Cl. .................. 514/314; 514/414; 514/423; 546/164; 546/169; 548/510; 548/540
[58] Field of Search .................. 548/540, 510; 514/423, 314, 414; 546/164, 169

[56] References Cited

U.S. PATENT DOCUMENTS 4,596,789 6/1986 Dutta et al. .................. 514/18
4,691,007 9/1987 Dutta et al. .................. 530/331

FOREIGN PATENT DOCUMENTS 0124317 11/1984 European Pat. Off. .
2678938 1/1993 France .
WO91/13907 9/1991 WIPO .

OTHER PUBLICATIONS

Tetrahedron Letters, vol. 34, No. 3, 1993, Oxford GB, pp. 381–384, V. Maggard et al., "A Convenient Synthesis of the Conformality . . . "

Tetrahedron Letters, vol. 34, No. 10, 1993, Oxford GB, pp. 1665–1668, J. E. Baldwin et al., "Synthesis of a Bicyclic Gamma–Lactam . . . "

*Primary Examiner*—Jacqueline Haley
*Attorney, Agent, or Firm*—Finnegan, Henderson, Farabow, Garrett & Dunner, L.L.P.

[57] ABSTRACT

Compounds of formula I

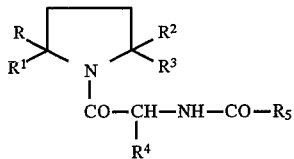

wherein the substituents are as defined herein, are disclosed as treatments for disorders linked to CCK and gastrin. Processes for preparing the compounds are also taught.

14 Claims, No Drawings

N-ACYL PYRROLIDINES AND DRUGS FOR THE TREATMENT OR PREVENTION OF CHOLECYSTOKININ AND GASTRIN-RELATED DISORDERS

This application is a National Stage application of PCT/FR94/00008, filed Jan. 3, 1994, and published on Jul. 21, 1994, as WO 94/15914.

The present invention relates to derivatives of formula:

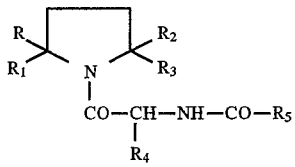

to their salts, to their preparation and to the medicaments containing them.

In the formula (I),

R represents a hydrogen atom or an alkyl, cycloalkyl or phenylalkyl radical or a phenyl radical optionally substituted by one or more substituents chosen from halogen atoms and alkyl and alkoxy radicals, $R_1$ represents an alkyl radical containing 1 to 12 carbon atoms in a straight or branched chain and optionally mono- or polyunsaturated, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted (by one or more substituents chosen from alkyl or alkoxy radicals or halogen atoms), a diphenylalkyl radical, a cinnamyl radical, a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals or a phenyl radical optionally substituted by one or more substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl or trifluoromethoxy radicals, $R_2$ represents a —$(CH_2)_n$—CO—$R_6$, —$(CH_2)_m$—O—CO—$R"_6$ or —$(CH_2)_m$—$NR_9R_{10}$ chain, an oxazolinyl radical optionally substituted by one or more alkyl radicals or a 3-alkyloxadiazolyl radical, $R_3$ represents a hydrogen atom or an alkyl or cycloalkyl radical or a phenylalkyl radical optionally substituted by one or more substituents chosen from halogen atoms and alkyl and alkoxy radicals, $R_4$ represents a hydrogen atom or an alkyl radical, $R_5$ represents a phenyl radical (optionally substituted by one or more substituents chosen from halogen atoms and alkyl, alkoxy and alkylthio radicals), a naphthyl radical, an indolyl radical, a quinolyl radical or a phenylamino radical in which the phenyl ring is optionally substituted by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—$SO_3H$ (in salt form), —CH=CH—alk', —C(=NOH)—COOX, —S—alk—COOX, —SO—alk—COOX, —$SO_2$—alk—COOX, —O—$CH_2$—alk'—COOX, —CX=N—O—alk—COOX, —alk—N(OH)—CO—alk, —alk—$SO_2H$, —$SO_2$—NH—CO—$R_{11}$, —$SO_2$—NH—$SO_2$—$R_{11}$, —CO—NH—CO—$R_{11}$, —CO—NH—$SO_2$—$R_{11}$, —B(OH)$_2$, —C(NH$_2$)=NOH, —$SO_2$—NH—$R_{12}$, —CO—NH—$R_{12}$,

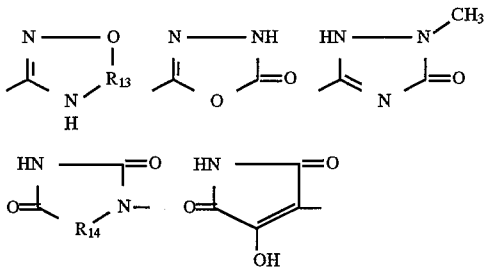

or 2,2-dimethyl-4,6-dioxo-1,3-dioxan-5-yl radicals, $R_6$ represents a hydroxyl, alkoxy, cycloalkyloxy, cycloalkylalkyloxy, phenyl or —$NR_9R_{10}$ radical, $R"_6$ represents an alkoxy, cycloalkyloxy, cycloalkylalkyloxy, phenyl or —$NR_9R_{10}$ radical, $R_7$ represents a hydrogen atom or an alkyl radical, a phenylalkyl radical or a phenyl radical optionally substituted by one or more substituents chosen from halogen atoms and alkyl, alkoxy and alkylthio radicals, $R_8$ represents an alkyl radical, a phenylalkyl radical or a phenyl radical optionally substituted by one or more substituents chosen from halogen atoms and alkyl, alkoxy and alkylthio radicals, or else $R_7$ and $R_8$ form, with the nitrogen atom to which they are attached, a saturated or unsaturated, mono- or polycyclic heterocycle containing 4 to 9 carbon atoms and one or more hetero atoms (O, N) and optionally substituted by one or more alkyl radicals, $R_9$ represents a hydrogen atom or an alkyl radical, a cycloalkylalkyl radical, a cycloalkyl radical, a phenylalkyl radical or a phenyl radical optionally substituted by one or more substituents chosen from halogen atoms and alkyl, alkoxy and alkylthio radicals, $R_{10}$ represents an alkyl radical, a cycloalkylalkyl radical, a cycloalkyl radical, a phenylalkyl radical or a phenyl radical optionally substituted by one or more substituents chosen from halogen atoms and alkyl, alkoxy and alkylthio radicals, or else $R_9$ and $R_{10}$ form, together with the nitrogen atom to which they are attached, a saturated or unsaturated, mono- or polycyclic heterocycle containing 4 to 9 carbon atoms and one or more hetero atoms (O, N, S) and optionally substituted by one or more alkyl radicals, $R_{11}$ represents an alkyl radical, a cycloalkyl radical, a trifluoromethyl radical or a phenyl radical optionally substituted by one or more substituents chosen from cyano, alkoxy, nitro or amino radicals and halogen atoms, $R_{12}$ represents a 5-tetrazolyl radical, $R_{13}$ represents C=O or S=O, $R_{14}$ represents O or C=O, n is equal to 0, 1 or 2, m is equal to 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, it being understood that n is other than 0 when R and $R_3$ each represent a hydrogen atom and $R_1$ represents a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals or a phenyl radical optionally substituted by one or more substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl or trifluoromethoxy radicals.

In the foregoing definitions and those which will be mentioned below, except when otherwise mentioned, the alkyl, alkylene and alkoxy radicals and the alkyl, alkylene and alkoxy portions contain 1 to 4 carbon atoms in a straight or branched chain, the acyl radicals or portions contain 2 to 4 carbon atoms and the cycloalkyl radicals and portions contain 3 to 6 carbon atoms.

When $R_1$ represents an unsaturated alkyl radical, the latter is preferably an isopropenyl radical.

When $R_1$ represents a cycloalkyl radical, the latter is preferably a cyclohexyl radical.

When $R_1$ represents an unsaturated cycloalkyl radical, the latter is preferably a tetrahydrophenyl, cyclopentadiene or dihydrophenyl radical.

When $R_1$ represents a polycycloalkyl radical, the latter is preferably a norbornyl or adamantyl radical.

When $R_1$ represents an unsaturated polycycloalkyl radical, the latter is preferably a norbornenyl radical.

When $R_7$ and $R_8$ form, with the nitrogen atom to which they are attached, a heterocycle, the latter is preferably a piperidino ring optionally substituted by one or more alkyl radicals or a 1,2,3,4-tetrahydroquinoline ring-system.

When $R_9$ and $R_{10}$ form, with the nitrogen atom to which they are attached, a heterocycle, the latter is preferably a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring-system, it being possible for these ring-systems to be optionally substituted by at least one alkyl radical.

The compounds of formula (I) containing one or more asymmetric centres have isomeric forms. These isomers also form part of the invention.

The compounds of formula (I) for which $R_5$ represents an optionally substituted phenylamino radical can be prepared by reacting a reactive derivative of carbamic acid, optionally obtained in situ by reacting a reactive derivative of carbonic acid, chosen from N,N'-carbonyldiimidazole, phosgene, diphosgene, triphosgene and p-nitrophenyl chloroformate, with a derivative of formula:

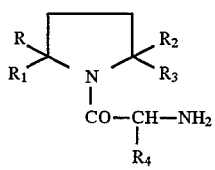
(II)

in which R, $R_1$, $R_2$, $R_3$ and $R_4$ have the same meanings as in the formula (I), with an aniline in which the phenyl ring is optionally substituted by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—$SO_3H$ (in salt form), —CH=CH—alk', —C(=NOH)—COOX, —S—alk—COOX, —SO—alk—COOX, —$SO_2$—alk—COOX, —O—$CH_2$—alk'—COOX, —CX=N—O—alk—COOX, —alk—N(OH)—CO—alk, —alk—$SO_2H$, —$SO_2$—NH—CO—$R_{11}$, —$SO_2$—NH—$SO_2$—$R_{11}$, —CO—NH—CO—$R_{11}$, —CO—NH—$SO_2$—$R_{11}$, —B(OH)$_2$, —C(NH$_2$)=NOH, —$SO_2$—NH—$R_{12}$, —CO—NH—$R_{12}$.

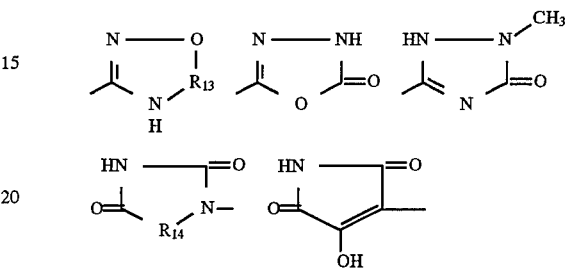

or 2,2-dimethyl-4,6-dioxo-1,3-dioxan-5-yl radicals.

This reaction is generally carried out in an inert solvent such as tetrahydrofuran, dimethylformamide, a chlorinated solvent (chloroform or 1,2-dichloroethane, for example) or an aromatic solvent (benzene or toluene, for example) or a mixture of these solvents, at a temperature between 20° C. and the boiling point of the solvent.

The reactive derivative of carbamic acid can be obtained under the same solvent and temperature conditions.

The derivatives of formula (II) can be obtained by deprotection of a derivative of formula:

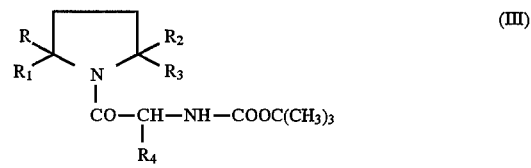
(III)

in which R, $R_1$, $R_2$, $R_3$ and $R_4$ have the same meanings as in the formula (I).

This deprotection is preferably carried out by means of iodotrimethylsilane or trifluoroacetic acid, in an inert solvent such as a chlorinated solvent (chloroform or 1,2-dichloroethane, for example) or acetonitrile, at a temperature between 15° and 40° C.

The derivatives of formula (III) for which $R_2$ represents a —(CH$_2$)$_n$—CO—$R_6$ chain and $R_6$ is not a hydroxyl radical can be obtained by reacting a derivative of formula:

(IV)

in which R, $R_1$ and $R_3$ have the same meanings as in formula (I) and $R_2$ has the same meanings as above, with an acid of formula:

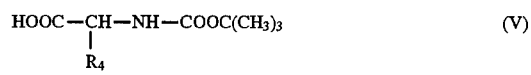
(V)

in which $R_4$ is defined as in the formula (I).

This reaction is carried out in an inert solvent such as acetonitrile, tetrahydrofuran or a chlorinated solvent, in the presence of a peptide condensing agent such as a carbodiimide (N,N'-dicyclohexylcarbodiimide for example) or an alkyl chloroformate, at a temperature between 10° and 40° C.

The derivatives of formula (V) can be obtained according to the usual methods for protection of amino acids.

The derivatives of formula (IV) for which $R_2$ represents a $-(CH_2)_n-CO-R_6$ chain and n is equal to 1 or 2 can be obtained by adaptation of the methods described by S. ROSSET et al., Tetrahedron Lett., 32, 7521 (1991); T. GALLAGHER et al., J. Chem. Soc. Perkin Trans. I, 2193 (1991) and J. F. W. KEANA, J. Org. Chem., 48, 2644 (1983).

The derivatives of formula (IV) for which R represents a hydrogen atom can be obtained by reduction of the compounds of formula:

(VI)

in which $R_1$ and $R_3$ have the same meanings as in the formula (I) and $R_2$ has the same meanings as in the formula (IV).

This reduction is generally carried out by means of hydrogen, in the presence of palladium on charcoal, in an inert solvent such as an alcohol or ethyl acetate, or by means of sodium borohydride in an alcohol, in the presence of an alkali metal carbonate, at a temperature between 20° C. and the boiling point of the reaction mixture.

The derivatives of formula (VI) for which $R_2$ represents a $-(CH_2)_n-CO-R_6$ radical, n is equal to 0, $R_6$ is not a hydroxyl radical and $R_3$ represents an alkyl, cycloalkyl or optionally substituted phenylalkyl radical can be obtained by reaction of a corresponding derivative of formula (VI) for which $R_3$ represents a hydrogen atom with a derivative of formula Hal-$R_3$ in which $R_3$ has the same meaning as above and Hal represents a halogen atom and preferably an iodine atom.

This reaction is generally carried out in an inert solvent such as tetrahydrofuran or ether, in the presence of a base such as sodium hydride or the sodium or lithium salt of hexamethyldisilazane, at a temperature between –78° C. and the boiling point of the reaction mixture.

The derivatives of formula (VI) for which $R_3$ represents a hydrogen atom and $R_2$ represents a $-(CH_2)_n-CO-R_6$ radical, n is equal to 0 and $R_6$ is not a hydroxyl radical can be obtained by deprotection and dehydration of a derivative of formula:

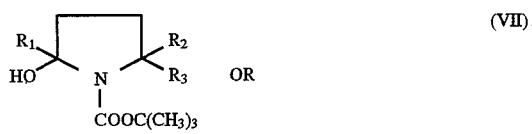

(VII)

OR

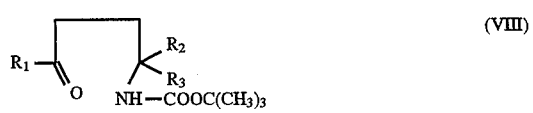

(VIII)

in which formulae $R_1$ has the same meanings as in the formula (I) and $R_2$ and $R_3$ have the same meanings as above, or a mixture of these derivatives.

These deprotection and dehydration operations are generally carried out by means of trifluoroacetic acid or iodotrimethylsilane, in an inert solvent such as a chlorinated solvent (dichloromethane for example), at a temperature in the region of 20° C.

The derivatives of formulae (VII) and (VIII) can be obtained by reaction of a derivative of formula:

(IX)

in which $R_1$ has the same meanings as above and $R_1$—M repesents an organomagnesium or organolithium derivative or a cuprate, with a derivative of formula:

(X)

in which $R_2$ and $R_3$ have the same meanings as above.

This reaction is carried out in an inert solvent such as tetrahydrofuran at a temperature between –78° C. and –20° C.

The derivatives of formula (X) can be obtained by reacting di-tert-butyl dicarbonate with a derivative of formula:

(XI)

in which $R_2$ and $R_3$ have the same meanings as above.

This reaction is generally carried out in the presence of triethylamine or 4-dimethylaminopyridine, in a chlorinated solvent such as dichloromethane, at a temperature in the region of 20° C.

The derivatives of formula (XI) are available on the market or can be obtained by esterification or amidation of pyroglutamic acid according to the methods described by M. HOLLOSI et al., Acta Chim. (Budapest), 71, 101 (1972); B. RIGO et al., J. Heterocycl. Chem., 25, 49 (1988); J. H. BILLMANN, J. L. RANDALL, J. Am. Chem. Soc., 66, 745 (1944); R. B. ANGIER, V. K. SMITH, J. Org. Chem., 21, 1540 (1956); J. C. SAUER, H. ADKINS, J. Am. Chem. Soc., 60, 402 (1938).

The derivatives of formula (IV) for which R represents an alkyl, cycloalkyl or phenylalkyl radical, or a phenyl radical optionally substituted by one or more substituents chosen from halogen atoms and alkyl and alkoxy radicals can be obtained by reaction of a corresponding derivative of formula (VI) with a derivative of formula:

(XII)

in which R has the same meanings as above and R—M represents an organolithium or organomagnesium derivative.

This reaction is carried out in an inert solvent such as tetrahydrofuran or ether, in the presence of a Lewis acid such as boron trifluoride or titanium tetrachloride, at a temperature between –78° C. and the boiling point of the reaction mixture.

The derivatives of formula (III) for which $R_2$ represents a $-(CH_2)_m-O-CO-R''_6$ chain can be obtained by reacting a derivative of formula:

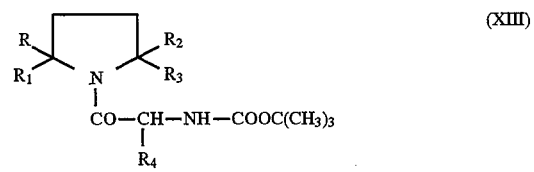

(XIII)

in which R, $R_1$, $R_3$ and $R_4$ have the same meanings as in the formula (I) and $R_{19}$ represents a $-(CH_2)_m-OH$ chain, with a halide of formula Hal—CO—R"$_6$ in which Hal represents a halogen atom, and preferably chlorine, and R"$_6$ has the same meanings as in the formula (I).

This reaction is carried out in an inert solvent such as a chlorinated solvent, in the presence of a trialkylamine, at a temperature between 20° C. and the boiling point of the reaction mixture.

The derivatives of formula (XIII) for which $R_{19}$ represents a —(CH$_2$)$_n$—OH chain can be obtained by reduction of a corresponding derivative of formula (III) for which $R_2$ represents a —CH$_2$)$_n$—CO—R$_6$ chain, n is equal to 0 or 1 and R$_6$ represents an alkoxy or a hydroxyl radical.

This reaction is carried out in an inert solvent such as an alcohol (methanol, ethanol or tert-butanol), tetrahydrofuran or a mixture of these solvents, in the presence of sodium borohydride or diborane, at a temperature between 20° C. and the boiling point of the reaction mixture.

The derivatives of formula (III) for which R$_2$ represents a —(CH$_2$)$_m$—O—CO—R"$_6$ chain. R"$_6$ represents an —NR$_9$R$_{10}$ radical and R$_9$ represents a hydrogen atom can also be obtained by condensation of a derivative of formula (XIII) in which R$_{19}$ represents a —(CH$_2$)$_m$—OH chain with an isocyanate of formula R$_{10}$NCO.

This reaction is carried out in an inert solvent such as a chlorinated solvent, tetrahydrofuran or dimethylformamide, optionally in the presence of a catalytic amount of an alkali metal alkoxide, at a temperature between 20° C. and the boiling point of the reaction mixture.

The derivatives of formula (III) for which R$_2$ represents a —(CH$_2$)$_m$—NR$_9$R$_{10}$ radical can be obtained by reacting an amine HNR$_9$R$_{10}$, in which R$_9$ and R$_{10}$ have the same meanings as in the formula (I), with a derivative of formula (XIII) in which R$_{19}$ represents a —(CH$_2$)$_m$—O—SO$_2$—CH$_3$ radical.

This reaction is generally carried out either in the presence of a large excess of amine at a temperature between 0° and 10° C. or, when the hydrochloride of the amine is used, in a chlorinated solvent in the presence of a trialkylamine at a temperature between 20° C. and the boiling point of the reaction mixture.

The derivatives of formula (XIII) in which R$_{19}$ represents a —(CH$_2$)$_m$—O—SO$_2$—CH$_3$ radical can be obtained by reaction of corresponding derivative of formula (XIII) for which R$_{19}$ represents a —(CH$_2$)$_m$—OH radical with methanesulphonyl chloride.

This reaction is generally carried out in an inert solvent such as acetonitrile or methylene chloride, in the presence of triethylamine, at a temperature between 0° C. and the boiling point of the reaction mixture.

The compounds of formula (III) for which R$_2$ represents a —(CH$_2$)$_n$—CO—R$_6$ radical and R$_6$ represents a hydroxyl radical can be obtained by saponification of a corresponding derivative of formula (III) for which R$_6$ represents an alkoxy radical.

This reaction is carried out in inert solvents such as tetrahydrofuran, methanol or dioxane and water, in the presence of a base such as sodium hydroxide, potassium hydroxide or lithium hydroxide, at a temperature between 0° and 25° C.

The derivatives of formula (III) for which R$_2$ repesents a —(CH$_2$)$_n$—CO—R$_6$ radical and R$_6$ represents an alkoxy, cycloalkoxy or cycloalkylalkyloxy radical can be obtained by esterification of the corresponding derivatives of formula (III) for which R$_2$ represents a —(CH$_2$)$_n$—CO—R$_6$ radical and R$_6$ represents a hydroxyl radical.

This reaction is preferably carried out by means of an alcohol R$_{16}$—OH in which R$_{16}$ represents an alkyl, cycloalkyl or cycloalkylalkyl radical, in the presence of tosyl chloride in pyridine, at a temperature between 0° and 25° C.

The derivatives of formula (III) for which R$_2$ represents a —CH$_2$)$_n$—CO—R$_6$ radical and R$_6$ represents a phenyl radical can be obtained by reacting a corresponding derivative of formula (III) for which R$_2$ represents a —(CH$_2$)$_n$—CO—R$_6$ radical and R$_6$ represents an alkoxy radical with phenylmagnesium bromide.

This reaction is preferably carried out in an inert solvent such as tetrahydrofuran or diethyl ether, at a temperature between –70° C. and the boiling point of the reaction mixture.

The compounds of formula (III) for which R$_2$ represents an optionally substituted oxazolinyl radical can be obtained by reacting a corresponding derivative of formula (III) for which R$_2$ represents a —(CH$_2$)$_n$—CO—R$_6$ radical, n is equal to 0 and R$_6$ represents a hydroxyl radical with 2-aminoethanol optionally substituted by one or more alkyl radicals.

This reaction is carried out in an inert solvent such as toluene, the water formed being removed, at the boiling point of the reaction mixture.

The compounds of formula (III) for which R$_2$ represents a 3-alkyloxadiazolyl radical can be obtained by reacting a corresponding derivative of formula (III) for which R$_2$ represents a —CH$_2$)$_n$—CO—R$_6$ radical, n is equal to 0 and R$_6$ represents an alkoxy radical with an alkaylamidoxime.

This reaction is carried out in an inert solvent such as tetrahydrofuran, in the presence of sodium hydride, at a temperature between 25° C. and the boiling point of the reaction mixture.

The derivatives of formula (III) for which R$_2$ represents a —(CH$_2$)$_n$—CO—R$_6$ chain and R$_6$ represents an —NR$_9$R$_{10}$ radical can be obtained by reacting a corresponding derivative of formula (III) for which R$_6$ represents a hydroxyl radical, or a reactive derivative of this acid, with an amine of formula HNR$_9$R$_{10}$.

When the acid is used, the reaction is carried out in the presence of a condensing agent used in peptide chemistry, such as a carbodiimide (for example N,N'-dicyclohexylcarbodiimide) or N,N'-carbonyldiimidazole, in an inert solvent such as an ether (tetrahydrofuran or dioxane, for example), an amide (N,N-dimethylformamide) or a chlorinated solvent (methylene chloride, 1,2-dichloroethane or chloroform, for example), at a temperature between 0° C. and the reflux temperature of the reaction mixture.

When a reactive derivative of the acid is used, it is possible to react the anhydride, a mixed anhydride or an ester (which can be chosen from the activated or non-activated esters of the acid).

The reaction is then carried out either in an organic medium, optionally in the presence of an acid-acceptor such as a nitrogenous organic base (trialkylamine, pyridine, 1,8-diazabicyclo[5.4.0]undec-7-ene or 1,5-diazabicyclo[4.3.0] non-5-ene, for example), in a solvent such as mentioned above or a mixture of these solvents, at a temperature between 0° C. and the reflux temperature of the reaction mixture, or in a two-phase aqueous-organic medium in the presence of an alkali metal or alkaline-earth metal base (sodium hydroxide, potassium hydroxide) or an alkali metal or alkaline-earth metal carbonate or bicarbonate at a temperature between 0° and 40° C.

The anilines, substituted where appropriate, are available on the market or can be obtained by application or adaptation of the methods described by R. SCHRÖTER, Methoden der organischen Chemie, Houben Weil, Volume XI/1, p 360;

G. J. ESSELEN et al., J. Am. Chem. Soc., 36, 322 (1914); G. ADRIANT et al., Bull. Soc. Chim. Fr., 1511 (1970); W. A. JACOBS et al., J. Am. Chem. Soc., 39, 2418 (1917) and J. Am. Chem. Soc., 39, 1435 (1917) and in the examples.

The compounds of formula (I) for which $R_5$ represents a phenylamino radical in which the phenyl ring is optionally substituted by one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'-COOX, —CX=N—O—alk—COOX, —alk—COOX or —alk'-COOX radicals in which X is other than a hydrogen atom can also be prepared by reacting a derivative of formula (II) with a phenyl isocyanate in which the phenyl ring is optionally substituted by one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O-CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'-COOX, —CX=N-O—alk—COOX, —alk—COOX or —alk'-COOX radicals in which X is other than a hydrogen atom.

This reaction is generally carried out in an inert solvent such as tetrahydrofuran, N,N-dimethylformamide, a chlorinated solvent (chloroform or 1,2-dichloroethane, for example) or an aromatic solvent (benzene or toluene, for example), at a temperature between 10° C. and the boiling point of the solvent.

The phenyl isocyanates are available on the market or can be obtained by application or adaptation of the methods described by R. RICHTER et al., The Chemistry of Cyanate and their Thio Derivatives, S. PATAI, Part 2, Wiley, New York (1977) and in the examples.

The compounds of formula (I) for which $R_5$ represents a naphthyl, indolyl, quinolyl or optionally substituted phenyl radical can be prepared by reaction of a derivative of formula (II) with an acid of formula HOOC-$R_5$ in which $R_5$ has the same meanings as above, or a reactive derivative of this acid.

When the acid is used, the reaction is carried out in the presence of a condensing agent used in peptide chemistry, such as a carbodiimide (for example N,N'-dicyclohexylcarbodiimide) or N,N'-carbonyldiimidazole, in an inert solvent such as an ether (tetrahydrofuran or dioxane, for example), an amide (dimethylformamide) or a chlorinated solvent (methylene chloride, 1,2-dichloroethane or chloroform, for example), at a temperature between 0° C. and the reflux temperature of the reaction mixture.

When a reactive derivative of the acid is used, it is possible to react the anhydride, a mixed anhydride or an ester (which can be chosen from the activated or nonactivated esters of the acid).

The reaction is then carried out either in an organic medium, optionally in the presence of an acid-acceptor such as a nitrogenous organic base (trialkylamine, pyridine, 1,8-diazabicyclo[5.4.0]undec-7-ene or 1,5-diazabicyclo[4.3.0] non-5-ene, for example), in a solvent such as mentioned above or a mixture of these solvents, at a temperature between 0° C. and the reflux temperature of the reaction mixture, or in a two-phase aqueous-organic medium in the presence of an alkali metal or alkaline-earth metal base (sodium hydroxide, potassium hydroxide) or an alkali metal or alkaline-earth metal carbonate or bicarbonate at a temperature between 0° and 40° C.

The compounds of formula (I) for which $R_5$ represents a phenylamino radical in which the phenyl ring is substituted by a carboxyl, —alk—COOH, —O—alk—COOH, —alk'-COOH, —CH=CH—COOH, —CO—COOH, —S—alk—COOH, —SO—alk—COOH, —$SO_2$—alk—COOH, —C(=NOH)-COOH, —O—$CH_2$—alk'-COOH or —CX=N-O—alk—COOH radical and/or $R_2$ represents a —$(CH_2)_n$-COOH chain can also be prepared by hydrolysis or, according to the situation, hydrogenolysis of the corresponding esters of formula (I).

When the alkyl or phenylalkyl esters are used, it is advantageous to carry out the hydrolysis by means of a base such as sodium hydroxide, potassium hydroxide or lithium hydroxide, in an inert solvent such as tetrahydrofuran, dioxane, water, methanol or a mixture of these solvents, at a temperature between 20° C. and 40° C. When phenylalkyl esters are used, it is can also be advantageous to carry out a hydrogenolysis by means of hydrogen or ammonium formate in the presence of a catalyst such as palladium on charcoal in a solvent such as methanol or ethyl acetate. When tert-butyl esters are used, it is advantageous to carry out the hydrolysis by means of an acid such as trifluoroacetic acid.

The compounds of formula (I) for which $R_5$ represents a phenylamino radical in which the phenyl ring is substituted by a hydroxyiminoalkyl or alkoxyiminoalkyl radical can also be prepared by reacting the corresponding acylated derivative of formula (I) with a derivative of formula:

$$H_2N—OR_{18} \qquad (XIV)$$

in which $R_{18}$ represents a hydrogen atom or an alkyl radical.

This reaction is generally carried out in an inert solvent such as an alcohol (methanol or ethanol, for example), water or a mixture of these solvents, at the boiling point of the solvent and optionally in the presence of a base such as pyridine.

The compounds of formula (I) for which $R_2$ represents a —$(CH_2)_n$—CO—$R_6$ chain, $R_6$ not being a hydroxyl radical, and $R_5$ represents a naphthyl, indolyl, quinolyl or optionally substituted phenyl radical or a phenylamino radical in which the phenyl ring is optionally substituted by one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O-CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'-COOX, —CX=N-O—alk—COOX, —alk—COOX or —alk'-COOX radicals in which X is other than a hydrogen atom can also be prepared by reacting a derivative of formula (IV) with an acid of formula:

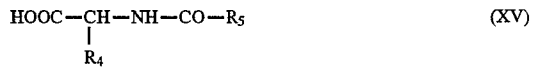

$$\text{HOOC—CH—NH—CO—}R_5 \qquad (XV)$$
$$\qquad\quad |$$
$$\qquad\;\; R_4$$

in which $R_5$ has the same meanings as above, or a reactive derivative of this acid, and $R_4$ has the same meanings as in the formula (I).

This reaction is preferably carried out in the presence of a condensing agent used in peptide chemistry, such as a carbodiimide, in a solvent such as acetonitrile, tetrahydrofuran or a chlorinated solvent, or by means of thionyl chloride in dichloromethane at a temperature between 10° C. and the boiling point of the solvent.

The acids of formula (XV) can be obtained by application or adaptation of the method described by J. R. JOHNSON et al., J. Am. Chem. Soc., 69, 2370 (1947) or, for the compounds for which $R_5$ represents an optionally substituted phenylamino radical, by reacting a phenyl isocyanate in which the phenyl ring is optionally substituted by one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'-COOX, —CX=N-O—alk—COOX, —alk—COOX or —alk'-COOX radicals in which X is other than a hydrogen atom with a derivative of formula:

(XVI)

in which $R_4$ has the same meanings as in the formula (I).

This reaction is generally carried out in aqueous solution in the presence of a base such as an alkali metal bicarbonate or in aqueous dioxane at a temperature in the region of 20° C.

It is understood, for a person skilled in the art that, the use of the processes according to the invention described above it may be necessary, in order to prevent side reactions, to introduce protective groups for the amine, alcohol, acid or ketone groups, such as those described by T. W. GREENE, Protective Groups in Organic Synthesis, John Wiley and Sons, New York. For example, the amine groups can be blocked in the form of tert-butyl or methyl carbamates, then regenerated by means of iodotrimethylsilane or of benzyl carbamates and then regenerated by hydrogenation after the process according to the invention has been carried out. The alcohol groups can, for example, be blocked in the form of a benzoate and then regenerated by hydrolysis in an alkaline medium after the process according to the invention has been carried out. The ketone groups can be blocked in the form of a 1,3-dioxolane and then regenerated by means of a hydrochloric acid/acetic acid mixture.

The enantiomers of the compounds of formula (I) containing at least one asymmetric site can be obtained by resolution of the racemates, for example by chromatography on a chiral column, or by synthesis from chiral precursors.

The compounds of formula (I) can be purified by standard known methods, for example by crystallization, chromatography or extractions.

The compounds of formula (I) containing a basic residue can optionally be converted to addition salts with an inorganic or organic acid by reacting with such an acid in an organic solvent such as an alcohol, a ketone, an ether or a chlorinated solvent.

The compounds of formula (I) containing an acid residue can optionally be converted to metal salts or to addition salts with nitrogenous bases according to methods known per se. These salts can be obtained by reacting a metal base (alkali metal or alkaline-earth metal base, for example), ammonia, an amine or a salt of an amine with a compound of formula (I) in a solvent. The salt formed is separated by standard methods.

These salts also form part of the invention.

Mention may be made, as examples of pharmaceutically acceptable salts, of the addition salts with inorganic or organic acids (such as acetate, propionate, succinate, benzoate, fumarate, maleate, oxalate, methanesulphonate, isethionate, theophyllineacetate, salicylate, methylenebis(β-hydroxynaphthoate), hydrochloride, sulphate, nitrate and phosphate), the salts with alkali metals (sodium, potassium or lithium) or with alkaline-earth metals (calcium or magnesium), the ammonium salt and the salts of nitrogenous bases (ethanolamine, trimethylamine, methylamine, benzylamine, N-benzyl-β-phenethylamine, choline, arginine, leucine, lysine or N-methylglucamine).

The compounds of formula (I) have advantageous pharmacological properties. These compounds have a strong affinity for cholecystokinin (CCK) receptors and gastrin receptors and are thus useful in the treatment and prevention of disorders linked to CCK and to gastrin affecting the nervous system and the gastrointestinal system.

These compounds can therefore be used for the treatment or prevention of psychoses, of anxiety disorders, of depression, of neurodegeneration, of panic attacks, of Parkinson's disease, of tardive dyskinesia, of irritable bowel syndrome, of acute pancreatitis, of ulcers, of disorders of intestinal motility, of certain tumours sensitive to CCK, as appetite regulators, in weaning from chronic treatments and alcohol or medicinal abuse and as constrictors of the pupil of the eye.

These compounds also have a potentiating effect on the analgesic activity of narcotic and non-narcotic medicaments. They can additionally have an analgesic effect of their own.

Moreover, the compounds having a strong affinity for CCK receptors modify memorizing capacity. These compounds can consequently be effective in memory disorders.

The affinity of the compounds of formula (I) for CCK receptors was determined according to a technique based on that of A. SAITO et al. (J. Neuro. Chem., 37, 483–490 (1981)) in the cerebral cortex and in the pancreas.

In these tests, the $IC_{50}$ of the compounds of formula (I) is generally less than or equal to 1000 nM.

Moreover, it is known that products which recognize the central receptors of CCK have a similar specificity for the gastrin receptors in the gastrointestinal tract (BOCK et al., J. Med. Chem., 32, 16–23 (1989); REYFELD et al., Am. J. Physiol., 240, G255–266 (1981); BEINFELD et al., Neuropeptides, 3, 411–427 (1983).

The compounds of formula (I) have low toxicity. Their subcutaneous $LD_{50}$ in mice is generally greater than 40 mg/kg.

The compounds of formula (I) for which R represents a hydrogen atom or an alkyl or phenyl radical, $R_1$ represents an alkyl or phenyl radical, $R_2$ represents a —$(CH_2)_n$—CO-$R_6$ chain, $R_3$ represents a hydrogen atom or an alkyl radical, $R_4$ represents an alkyl radical, $R_5$ represents a phenylamino radical in which the phenyl ring is substituted by a carboxyl radical, $R_6$ represents an alkoxy radical and n is equal to 0, their salts and their isomers are particularly advantageous.

The following compounds, their salts and their isomers are particularly advantageous: (S)-3-3-2-(2-tert-butoxycarbonyl-5,5-diphenyl-1-pyrrolidinyl)-2-oxoethyl]ureido}benzoic acid, (2S,5R)-3-3-2-(2-tert-butoxycarbonyl-5-methyl-5-phenyl-1-pyrrolidinyl)-2-oxoethyl]ureido}benzoic acid, (2RS,5SR)-3-3-2-(2-tert-butoxycarbonyl-2-methyl-5-phenyl-1-pyrrolidinyl)-2-oxoethyl]ureido}benzoic acid, (2S,5S)-3-3-2-(2-tert-butoxycarbonyl-5-butyl-1-pyrrolidinyl)-2-oxoethyl]ureido}benzoic acid.

The examples which follow illustrate the invention without limiting it.

EXAMPLE 1

A To a solution of 2 g of tert-butyl (S)-1-{2-[3-(3-(benzyloxycarbonyl)phenyl)ureido]acetyl}-5,5-diphenylpyrrolidine-2-carboxylate in 100 cm$^3$ of ethyl acetate, there is added 0.2 g of 10% palladium-on-charcoal. The suspension is stirred for twenty hours at a temperature in the region of 20° C. under a hydrogen atmosphere (130 kPa). The catalyst is separated by filtration through Celite and rinsed with 50 cm$^3$ of ethyl acetate and the filtrate is concentrated to dryness under reduced pressure. The residue is chromatographed on silica [eluent: dichloromethane/methanol (90/10 by volume)]. The fractions containing the expected product are combined and concentrated under reduced pressure. The residue is resuspended in 10 cm$^3$ of diisopropyl ether, filtered off and dried under vacuum at a temperature in the region of 40° C. There is thus obtained 0.65 g of (S)-3-3-2-(2-tert-butoxycarbonyl-5,5-diphenyl-1-pyrrolidinyl)-2-oxoethyl]ureido}benzoic acid melting at 180° C.; Rf=0.22 [TLC on silica, eluent: dichloromethane/methanol (90/10 by volume)].

B tert-Butyl (S)-1-{2-[3-(3-(benzyloxycarbonyl)phenyl)ureido]acetyl}-5,5-diphenylpyrrolidine-2-carboxylate can be obtained in the following way: to a solution of 2.8 g of tert-butyl (S)-5,5-diphenyl-1-(2-phthalimidoacetyl)pyrrolidine-2-carboxylate in 50 cm$^3$ of dichloromethane, there is added, at a temperature in the region of 5° C. 0.9 cm$^3$ of methylhydrazine. The reaction mixture is maintained at a temperature in the region of 5° C. for twenty hours and then heated to reflux for four hours. After cooling to a temperature in the region of 20° C. the organic phase is washed with twice 50 cm$^3$ of water, dried over magnesium sulphate and concentrated under reduced pressure. The residue is diluted with 50 cm$^3$ of tetrahydrofuran, then to this is added 1.4 g of benzyl 3-isocyanatobenzoate. The reaction mixture is stirred for twenty hours at a temperature in the region of 20° C. and then concentrated under reduced pressure. The residue is purified by chromatography on silica [eluent: cyclohexane/ethyl acetate (70/30 by volume)]. The fractions containing the expected product are combined and concentrated under reduced pressure. There are thus obtained 2 g of tert-butyl (S)-1-{2-[3-(3-(benzyloxycarbonyl)phenyl)ureido]acetyl}-5,5-diphenylpyrrolidine-2-carboxylate in the form of a foam, which is used as is in the subsequent syntheses.

C tert-Butyl (S)-5,5-diphenyl-1-(2-phthalimido-acetyl)pyrrolidine-2-carboxylate can be prepared in the following way: to a solution of 1 g of tert-butyl (S)-5,5-diphenylpyrrolidine-2-carboxylate in 30 cm$^3$ of 1,4-dioxane, there is added, at a temperature in the region of 20° C., 0.25 cm$^3$ of pyridine, then a solution of 0.7 g of phthaloylglycine chloride in 20 cm$^3$ of 1,4-dioxane. The reaction mixture is stirred for twenty hours at a temperature in the region of 20° C. and then concentrated under reduced pressure. The residue is dissolved in 100 cm$^3$ of ethyl acetate and the organic phase is washed with twice 50 cm$^3$ of distilled water, dried over magnesium sulphate and concentrated under reduced pressure. The residue is purified by chromatography on silica [eluent: cyclohexane/ethyl acetate (70/30 by volume)]. The fractions containing the expected product are combined and concentrated under reduced pressure. There is thus obtained 1 g of tert-butyl (S)-5,5-diphenyl-1-(2-phthalimidoacetyl)pyrrolidine-2-carboxylate in the form of a foam, which is used as is in the subsequent synthesis.

D tert-Butyl (S)-5,5-diphenylpyrrolidine-2-carboxylate can be prepared in the following way: to a solution of 4.95 g of tert-butyl (S)-5-phenyl-$\Delta^5$-pyrroline-2-carboxylate in 100 cm$^3$ of tetrahydrofuran, there are added, at a temperature in the region of 0° C., 2.5 cm$^3$ of boron trifluoride etherate. The mixture is stirred for thirty minutes at a temperature in the region of 0° C. and then 11 cm$^3$ of a 2M solution of phenyllithium in an ether/hexane mixture are added over thirty minutes at a temperature in the region of –70° C. The reaction mixture is stirred for four hours at a temperature in the region of –50° C. and then poured into 200 cm$^3$ of a saturated aqueous ammonium chloride solution. The aqueous phase is extracted with three times 100 cm$^3$ of ethyl acetate. The organic extracts are combined and washed with twice 100 cm$^3$ of water, dried over magnesium sulphate and concentrated under reduced pressure. The residue is purified by chromatography on silica [eluent: petroleum ether/diethyl ether (70/30 by volume)]. The fractions containing the expected product are combined and concentrated under reduced pressure. There is thus obtained 1 g of tert-butyl (S)-5,5-diphenylpyrrolidine-2-carboxylate in the form of an oil, which is used as is in the subsequent syntheses.

E tert-Butyl (S)-5-phenyl-$\Delta^5$-pyrroline-2 2-carboxylate can be prepared in the following way: to a solution of 1.8 g of tert-butyl (S)-2-tert-butoxycarbonylamino-5-oxo-5-phenylpentanoate in 25 cm$^3$ of dichloromethane, there are added, at a temperature in the region of 20° C., 2.3 cm$^3$ of trifluoroacetic acid. The reaction mixture is stirred for six hours at a temperature in the region of 20° C. then 120 cm$^3$ of a saturated aqueous sodium hydrogen carbonate solution are added. The organic phase is separated after settling has taken place, washed with 20 cm$^3$ of distilled water, dried over magnesium sulphate and concentrated under reduced pressure. There is thus obtained 0.9 g of tert-butyl (S)-5-phenyl-$\Delta^5$-pyrroline-2-carboxylate in the form of an oil, which is used as is in the subsequent synthesis.

F tert-Butyl (S)-2-tert-butoxycarbonylamino-5-oxo-5-phenylpentanoate can be prepared in the following way: to a suspension of 0.72 g of magnesium in 20 cm$^3$ of tetrahydrofuran, there is added over thirty minutes, at a temperature between 20° and 30° C., a solution of 2.8 cm$^3$ of bromobenzene in 60 cm$^3$ of tetrahydrofuran. The reaction mixture is kept stirring at a temperature in the region of 24° C. for one hundred and forty-five minutes, and is then added over twenty minutes to a solution of 5.7 g of tert-butyl (S)-1-tert-butoxycarbonyl-5-oxopyrrolidine-2-carboxylate in 80 cm$^3$ of tetrahydrofuran maintained at a temperature in the region of –75° C. The reaction mixture is stirred for a further three hours at a temperature in the region of –78° C. and then warmed to a temperature in the region of –15° C. There are then added over fifteen minutes 100 cm$^3$ of a 10% aqueous ammonium chloride solution. The aqueous phase is separated after settling has taken place and extracted with three times 100 cm$^3$ of diethyl ether. The organic phases are combined and washed with twice 25 cm$^3$ of water, dried over magnesium sulphate and concentrated under reduced pressure at a temperature in the region of 50° C. The residue is purified by recrystallization from 20 cm$^3$ of pentane. There are thus obtained 2.5 g of tert-butyl (S)-2-tert-butoxycarbonylamino-5-oxo-5-phenylpentanoate melting at 107° C. This product can also take the form of tert-butyl (2S,5RS)-1-tert-butoxycarbonyl-5-hydroxy-5-phenylpyrrolidine-2-carboxylate melting at 85° C.

tert-Butyl (S)-1-tert-butoxycarbonyl-5-oxo-pyrrolidine-2-carboxylate can be obtained according to the method described by J. ACKERMANN and M. MATTHES, Helv. Chim. Acta, 73, 122–132, (1990).

G Benzyl 3-isocyanatobenzoate can be prepared in the following way: to a suspension of 2 g of charcoal in a mixture of 12.5 cm³ of trichloromethyl chloroformate and 50 cm³ of toluene, there is added over fifteen minutes, at a temperature in the region of −25° C., a solution of benzyl 3-aminobenzoate in 150 cm³ of toluene, prepared by neutralizing 27 g of benzyl 3-aminobenzoate hydrochloride with 14.4 cm³ of triethylamine in 150 cm³ of toluene and filtering the suspension thus obtained. The reaction mixture is stirred at a temperature in the region of 25° C. for two hours, then heated at a temperature in the region of 110° C. for two hours. After cooling to a temperature in the region of 25° C. the reaction mixture is degassed by bubbling nitrogen through it, filtered through filter paper and concentrated under reduced pressure at a temperature in the region of 52° C. There are thus obtained 27 g of benzyl 3-isocyanatobenzoate in the form of an oil, which is used as is in the subsequent syntheses.

Benzyl 3-aminobenzoate can be prepared according to the method described by H. A. SHONLE et al., J. Amer. Chem. Soc., 43, 361 (1921).

Phthaloylglycine chloride can be prepared according to the method described by W. GRASSMANN and E. SCHULTE-UERBING, Chem. Ber., 83, 244 (1950).

EXAMPLE 2

A To a solution of 0.55 g of tert-butyl (2S,5R)-1-{2-[3-(3-(benzyloxycarbonyl)phenyl)ureido]acetyl}-5-methyl-5-phenylpyrrolidine-2-carboxylate in 100 cm³ of ethyl acetate, there is added 0.05 g of 10% palladium-on-charcoal. The suspension is stirred for 20 hours at a temperature in the region of 20° C. under a hydrogen atmosphere (130 kPa). The catalyst is separated by filtration through Celite and rinsed with 50 cm³ of ethyl acetate and the filtrate is concentrated to dryness under reduced pressure. The residue is chromatographed on silica [eluent: dichloromethane/methanol (90/10 by volume)]. The fractions containing the expected product are combined and concentrated under reduced pressure. The residue is resuspended in 10 cm³ of petroleum ether, filtered off and dried under vacuum at a temperature in the region of 40° C. There is thus obtained 0.3 g of (2S,5R)-3-3-2-(2-tert-butoxycarbonyl-5-methyl-5-phenyl-1-pyrrolidinyl)-2-oxoethyl]ureido}benzoic acid; Rf=0.16 [TLC on silica, eluent:dichloromethane/methanol (90/10 by volume)].

B tert-Butyl (2S,5R)-1-{2-[3-(3-(benzyloxycarbonyl)phenyl)ureido]acetyl}-5-methyl-5-phenylpyrrolidine-2-carboxylate can be prepared in the following way: to a solution of 0.5 g of tert-butyl (2S,5R)-5-methyl-5-phenylpyrrolidine-2-carboxylate and 0.63 g of 2-{3-[3-(benzyloxycarbonyl)phenyl]ureido}acetic acid in 50 cm³ of acetonitrile, there is added, at a temperature in the region of 20° C. 0.4 g of N,N'-dicyclohexylcarbodiimide. The reaction mixture is stirred for twenty hours at a temperature in the region of 20° C., concentrated under reduced pressure, taken up in 25 cm³ of ethyl acetate, filtered and rinsed with 5 cm³ of ethyl acetate. The filtrate is concentrated under reduced pressure and the residue purified by chromatography on silica [eluent: cyclohexane/ethyl acetate (70/30 by volume)]. The fractions containing the expected product are combined and concentrated under reduced pressure. There is thus obtained 0.55 g of tert-butyl (2S,5R)-1-{2-[3-(3-(benzyloxycarbonyl)phenyl)ureido]acetyl}-5-methyl-5-phenylpyrrolidine-2-carboxylate in the form of a foam, which is used as is in the subsequent syntheses.

C tert-Butyl (2S,5R)-5-methyl-5-phenylpyrrolidine-2-carboxylate can be prepared as described in Example 1 D, but starting from 4.35 g of tert-butyl (S)-5-phenyl-Δ⁵-pyrroline-2-carboxylate, 2.5 cm³ of boron trifluoride etherate and 13.75 cm³ of a 1.6M solution of methyllithium in diethyl ether, in 100 cm³ of tetrahydrofuran. After treatment, there is obtained 0.5 g of tert-butyl (2S,5R)-5-methyl-5-phenylpyrrolidine-2-carboxylate in the form of an oil, which is used as is in the subsequent syntheses.

D 2-{3-[3-(Benzyloxycarbonyl)phenyl]ureido}acetic acid can be prepared in the following way: to a solution of 3.97 g of glycine and 14.62 g of potassium carbonate in 90 cm³ of water, there is added over fifteen minutes 13.4 g of benzyl 3-isocyanatobenzoate in solution in 70 cm³ of 1,4-dioxane. The reaction mixture is stirred for four hours at a temperature in the region of 20° C., then acidified to pH 1 with a 4N aqueous hydrochloric acid solution. The insoluble product is separated by filtration, washed with three times 50 cm³ of water and air-dried. There are thus obtained 13 g of 2-{3-[3-(Benzyloxycarbonyl)phenyl]ureido}acetic acid, which is used as is in the subsequent syntheses.

EXAMPLE 3

A The reaction is carried out in a way similar to that described in Example 1A but starting from 0.54 g of tert-butyl (2RS,5SR)-1-{2-[3-(3-(benzyloxycarbonyl)phenyl)ureido]acetyl}-2-methyl-5-phenyl-pyrrolidine-2-carboxylate and 0.15 g of 10% palladium-on-charcoal in 30 cm³ of ethyl acetate. After treatment, there is obtained 0.25 g of (2RS,5SR)-3-3-2-(2-tert-butoxycarbonyl-2-methyl-5-phenyl-1-pyrrolidinyl)-2-oxoethyl]ureido}benzoic acid melting at 150° C.

B tert-Butyl (2RS,5SR)-1-{2-[3-(3-(benzyloxycarbonyl)phenyl)ureido]acetyl}-2-methyl-5-phenylpyrrolidine-2-carboxylate can be prepared as described in Example 2 B, but starting from 0.80 g of tert-butyl (2RS,5SR)-2-methyl-5-phenylpyrrolidine-2-carboxylate, 1.0 g of 2-{3-[3-(benzyloxycarbonyl)phenyl]ureido}acetic acid and 0.63 g of N,N'-dicyclohexylcarbodiimide in 25 cm³ of acetonitrile. After treatment, there is obtained 0.6 g of tert-butyl (2RS,5SR)-1-{2-[3-(3-(benzyloxycarbonyl)phenyl)ureido]acetyl}-2-methyl-5-phenylpyrrolidine-2-carboxylate in the form of an oil, which is used as is in the subsequent syntheses.

C tert-Butyl (2RS,5SR)-2-methyl-5-phenylpyrrolidine-2-carboxylate can be prepared in the following way: to a suspension of 5.0 g of tert-butyl (RS)-2-methyl-5-phenyl-Δ⁵-pyrroline-2-carboxylate in a mixture of 15 cm³ of ethanol and 7.5 cm³ of distilled water, there is added, at a temperature in the region of 5° C., a solution of 0.76 g of sodium borohydride and 0.35 g of sodium carbonate in 5 cm³ of distilled water. The mixture is stirred for sixty hours at a temperature in the region of 20° C. and is then diluted with 150 cm³ of distilled water. The aqueous phase is extracted with twice 100 cm³ of dichloromethane and the combined extracts are washed with 50 cm³ of distilled water, dried over magnesium sulphate and concentrated under reduced pressure. The residue is purified by chromatography on silica [eluent: dichloromethane, then dichloromethane/methanol (99/1 by volume)]. The fractions containing the expected product are combined and concentrated under reduced pressure. There is thus obtained 0.9 g of tert-butyl (2RS,5SR)-2-methyl-5-phenylpyrrolidine-2-carboxylate in the form of an oil, which is used as is in the subsequent synthesis.

D tert-Butyl (RS)-2-methyl-5-phenyl-Δ⁵-pyrroline-2-carboxylate can be obtained in the following way: to a suspension of 1.6 g of 50% sodium hydride in petroleum jelly in 50 cm³ of tetrahydrofuran, there is added dropwise a solution of 7.5 g of tert-butyl (S)-5-phenyl-$\Delta^5$-pyrroline-2-carboxylate in 150 cm$^3$ of tetrahydrofuran. The mixture is stirred for four hours at a temperature in the region of 25° C. and 2.05 cm$^3$ of methyl iodide are then added. The reaction mixture is stirred for eighteen hours at a temperature in the region of 25° C. and then 5 cm$^3$ of distilled water are added. The mixture is concentrated under reduced pressure and diluted with 200 cm$^3$ of a 15% aqueous sodium chloride solution. The aqueous phase is extracted with three times 100 cm$^3$ of dichloromethane. The organic extracts are combined and washed with twice 100 cm$^3$ of distilled water, dried over magnesium sulphate while treating with 3S charcoal and concentrated under reduced pressure. There are thus obtained 5.1 g of tert-butyl (RS)-2-methyl-5-phenyl-$\Delta^5$-pyrroline-2-carboxylate in the form of an oil, which solidifies and is used as is in the subsequent syntheses.

EXAMPLE 4

A The reaction is carried out in a way similar to that described in Example 1 A, but starting from 2.4 g of tert-butyl (2S,5S)-1-2-3-(3-(benzyloxycarbonyl)phenyl) ureido]acetyl}-5-butylpyrrolidine-2-carboxylate and 0.25 g of 10% palladium-on-charcoal in 100 cm$^3$ of ethanol. After treatment, there is obtained 1 g of (2S,5S)-3-3-2-(2-tert-butoxycarbonyl-5-butyl-1-pyrrolidyl)-2-oxoethyl] ureido}benzoic acid; $[\alpha]_D^{20}$=38.4° (c=10; methanol):

B tert-Butyl (2S,5S)-1-{2-[3-(3-(benzyloxycarbonyl) phenyl)ureido]acetyl}-5-butylpyrrolidine-2-carboxylate can be prepared as described in Example 2 B, but from 1.15 g of tert-butyl (2S,5S)-5-butylpyrrolidine-2-carboxylate, 1.65 g of 2-{3-[3-(benzyloxycarbonyl)phenyl]ureido}acetic acid and 1.05 g of N,N'-dicyclohexylcarbodiimide in 25 cm$^3$ of acetonitrile. After treatment, there are obtained 2.4 g of tert-butyl (2S,5S)-1-{2-[3-(3-(benzyloxycarbonyl)phenyl) ureido]acetyl}-5-butylpyrrolidine-2-carboxylate in the form of a foam, which is used as is in the subsequent syntheses.

C tert-Butyl (2S,5S)-5-butylpyrrolidine-2-carboxylate can be prepared in the following way: to a solution of 1.3 g of tert-butyl (S)-5-butyl-$\Delta^5$-pyrroline-2-carboxylate in 50 cm$^3$ of ethanol, there is added 0.05 g of platinum oxide. The suspension is stirred for twenty hours at a temperature in the region of 20° C. under a hydrogen atmosphere (130 kPa). The catalyst is separated by filtration through Celite and rinsed with 50 cm$^3$ of ethanol and the filtrate is concentrated to dryness under reduced pressure. There are thus obtained 1.2 g of tert-butyl (2S,5S)-5-butylpyrrolidine-2-carboxylate in the form of an oil, which is used as is in the subsequent syntheses.

D tert-Butyl (S)-5-butyl-$\Delta^5$-pyrroline-2-carboxylate can be prepared as described in Example 1 E, but starting from 2 g of tert-butyl (S)-2-tert-butoxycarbonylamino-5-oxononanoate and 2.65 cm$^3$ of trifluoroacetic acid in 75 cm$^3$ of chloroform. After treatment, there is obtained 0.6 g of tert-butyl (S)-5-butyl-$\Delta^5$-pyrroline-2-carboxylate in the form of an oil, which is used as is in the subsequent syntheses.

E tert-Butyl (S)-2-tert-butoxycarbonylamino-5-oxononanoate can be prepared in the following way: to a mixture of 9.6 cm$^3$ of a 2.5M solution of butyllithium in hexanes and 10 cm$^3$ of tetrahydrofuran, there is added over thirty minutes, at a temperature in the region of −50° C., a solution of 5.71 g of tert-butyl (S)-1-tert-butoxycarbonyl-5-oxopyrrolidine-2-carboxylate in 30 cm$^3$ of tetrahydrofuran. The reaction mixture is stirred for a further eight hours at a temperature in the region of −50° C. then warmed to a temperature in the region of 20° C. and stirred for sixteen hours. The mixture is then poured into 100 cm$^3$ of a saturated aqueous ammonium chloride solution. The aqueous phase is extracted with twice 50 cm$^3$ of ethyl acetate. The organic phases are combined, washed with twice 50 cm$^3$ of distilled water, dried over magnesium sulphate and concentrated under reduced pressure. The residue is purified by chromatography on silica [eluent: cyclohexane/ethyl acetate (70/30 by volume)]. The fractions containing the expected product are combined and concentrated under reduced pressure. There are thus obtained 2 g of tert-butyl (S)-2-tert-butoxycarbonylamino-5-oxononanoate in the form of an oil, which is used as is in the subsequent syntheses.

EXAMPLE 5

A The reaction is carried out in a way similar to that described in Example 1 A, but starting from 1.65 g of tert-butyl (2S,5R)-1-{2-[3-(3-(benzyloxycarbonyl)phenyl) ureido]acetyl}-5-isobutylpyrrolidine-2-carboxylate and 0.25 g of 10% palladium-on-charcoal in 50 cm$^3$ of ethanol. After treatment, there is obtained 0.57 g of (2S,5R)-3-3-2-(2-tert-butoxycarbonyl-5-isobutyl-1-pyrrolidinyl)-2-oxoethyl]ureido}benzoic acid, the optical rotation of which is $[\alpha]_D^{20}$=−36.8° (c=1.0; methanol).

B tert-Butyl (2S,5R)-1-{2-[3-(3-(benzyloxycarbonyl) phenyl)ureido]acetyl}-5-isobutylpyrrolidine-2-carboxylate can be prepared as described in Example 2 B, but starting from 1.9 g of tert-butyl (2S,5R)-5-isobutylpyrrolidine-2-carboxylate, 2.75 g of 2-{3-[3-(benzyloxycarbonyl)phenyl] ureido}acetic acid and 1.73 g of N,N'-dicyclohexylcarbodiimide in 75 cm$^3$ of acetonitrile. After treatment, there are obtained 1.65 g of tert-butyl (2S,5R)-1-{2-[3-(3-(benzyloxycarbonyl)phenyl)ureido]acetyl}-5-isobutylpyrrolidine-2-carboxylate in the form of a foam used, which is as is in the subsequent syntheses.

C tert-Butyl (2S,5R)-5-isobutylpyrrolidine-2-carboxylate can be prepared as described in Example 4 C, but starting from 1.9 g of tert-butyl (S)-5-isobutyl-$\Delta^5$-pyrroline-2-carboxylate and 0.2 g of platinum oxide in 50 cm$^3$ of ethanol. After treatment, there are obtained 1.9 g of tert-butyl (2S,5R)-5-isobutylpyrrolidine-2-carboxylate in the form of an oil, which is used as is in the subsequent syntheses.

D tert-Butyl (S)-5-isobutyl-$\Delta^5$-pyrroline-2-carboxylate can be prepared as described in Example 1 E, but starting from 3 g of tert-butyl (S)-2-tert-butoxycarbonylamino-7-methyl-5-oxooctanoate and 4 cm$^3$ of trifluoroacetic acid in 100 cm$^3$ of chloroform. After treatment, there are obtained 1.9 g of tert-butyl (S)-5-isobutyl-$\Delta^5$-pyrroline-2-carboxylate in the form of an oil, which is used as is in the subsequent syntheses.

E tert-Butyl (S)-2-tert-butoxycarbonylamino-7-methyl-5-oxooctanoate can be prepared as described in Example 1 F, but starting from 4.3 g of tert-butyl (S)-1-tert-butoxycarbonyl-5-oxopyrrolidine-2-carboxylate, 2.12 cm$^3$ of isobutyl bromide and 0.54 g of magnesium in 90 cm$^3$ of tetrahydrofuran. After treatment, there are obtained 3 g of tert-butyl (S)-2-tert-butoxycarbonylamino-7-methyl-5-oxooctanoate in the form of an oil, which is used as is in the subsequent syntheses.

The medicaments according to the invention consist of a compound of formula (I) in free form or in the form of a pharmaceutically acceptable salt, in the pure state or in the form of a composition in which it is combined with any other pharmaceutically compatible product, which can be inert or physiologically active. The medicaments according to the invention can be employed orally, parenterally, rectally or topically.

As solid compositions for oral administration, tablets, pills, powders (gelatin capsules or wafer capsules) or granules can be used. In these compositions, the active principle according to the invention is mixed with one or more inert diluents such as starch, cellulose, sucrose, lactose or silica, under an argon stream. These compositions can also comprise substances other than diluents, for example one or more lubricating agents such as magnesium stearate or talc, a colouring agent, a coating agent (dragées) or varnish.

As liquid compositions for oral administration, pharmaceutically acceptable solutions, suspensions, emulsions, syrups and elixirs containing inert diluents such as water, ethanol, glycerol, vegetable oils or paraffin oil can be used. These compositions can comprise substances other than diluents, for example wetting, sweetening, thickening, flavouring or stabilizing substances.

The sterile compositions for parenteral administration can preferably be suspensions, emulsions or aqueous or non-aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, tonicity, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eye drops, mouthwashes, nose drops or aerosols.

In human therapy, the compounds according to the invention are particularly useful in the treatment and prevention of disorders linked to CCK and to gastrin affecting the nervous system and the gastrointestinal system. These compounds can thus be used in the treatment and prevention of psychoses, of anxiety disorders, of depression, of neurodegeneration, of panic attacks, of Parkinson's disease, of tardive dyskinesia, of irritable bowel syndrome, of acute pancreatitis, of ulcers, of disorders of intestinal motility, of certain tumours sensitive to CCK, of memory disorders, in weaning from chronic treatments and alcohol or medicinal abuse, as constrictors of the pupil of the eye, as analgesics, as potentiating agents of the analgesic activity of narcotic and non-narcotic analgesic medicaments and as appetite regulators.

The doses depend on the desired effect, on the duration of treatment and on the administration route used; they are generally between 0.05 g and 1 g per day orally for an adult with single doses ranging from 10 mg to 500 mg of active substance.

Generally, the doctor will determine the appropriate dosage in accordance with the age, the weight and all the other factors specific to the subject to be treated.

The following examples illustrate compositions according to the invention:

EXAMPLE A

Hard gelatin capsules containing 50 mg of active product and which have the following composition are prepared according to the usual technique:

| | |
|---|---|
| 3-3-2-(2-tert-Butoxycarbonyl-5,5-diphenyl-1-pyrrolidinyl)-2-oxoethyl]ureido)benzoic acid | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing 50 mg of active product and which have the following composition are prepared according to the usual technique:

| | |
|---|---|
| 3-3-2-(2-tert-Butoxycarbonyl-5-methyl-5-phenyl-1-pyrrolidinyl)-2-oxoethyl]ureido}benzoic acid | 50 mg |
| Lactose | 104 mg |
| Cellulose | 40 mg |
| Povidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) q.s. 1 finished film-coated tablet weighing | 245 mg |

EXAMPLE C

An injectable solution containing 10 mg of active product and which has the following composition is prepared:

| | |
|---|---|
| 3-3-2-(2-tert-Butoxycarbonyl-5-methyl-5-phenyl-1-pyrrolidinyl)-2-oxoethyl]ureido}benzoic acid | 10 mg |
| Benzoic acid | 80 mg |
| Benzyl alcohol | 0.06 cm³ |
| Sodium benzoate | 80 mg |
| 95% Ethanol | 0.4 cm³ |
| Sodium hydroxide | 24 mg |
| Propylene glycol | 1.6 cm³ |
| Water q.s. | 4 cm³ |

We claim:

1. A compound of formula (I):

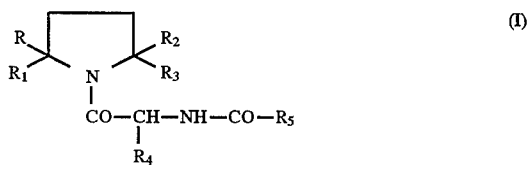

in which:

R represents a hydrogen atom or an alkyl, cycloalkyl or phenylalkyl radical or a phenyl radical optionally substituted by at least one substituent, said substituent being a halogen atom or an alkyl or alkoxy radical, $R_1$ represents an alkyl radical containing 1 to 12 carbon atoms in a straight or branched chain and optionally mono- or polyunsaturated, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted by at least one substituent, said substituent being an alkyl radical, an alkoxy radical, a halogen atom, a diphenylalkyl radical, a cinnamyl radical, a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals or a phenyl radical optionally substituted by at least one substituent, said substituent being a halogen atom or an alkyl, alkoxy, hydroxyl, nitro, amino, monoalkylamino, dialkylamino, alkoxycarbonyl, —CO—NR$_7$R$_8$, —NH—CO—CH$_3$, trifluoromethyl or trifluoromethoxy radical, R$_2$ represents a —(CH$_2$)$_n$—CO—R$_6$, —(CH$_2$)$_m$—O—CO—R"$_6$ or —(CH$_2$)$_m$—NR$_9$R$_{10}$ chain, an oxazolinyl radical optionally substituted by one or more alkyl radicals, or a 3-alkyloxadiazolyl radical, R$_3$ represents a hydrogen atom or an alkyl or cycloalkyl radical or a phenylalkyl radical optionally substituted with at least one substituent, said substituent being a halogen atom or an alkyl or alkoxy radical, R$_4$ represents a hydrogen atom or an alkyl radical, R$_5$ represents a phenyl radical optionally substituted by at least one substituent, said substituent being a halogen atom, or an alkyl, alkoxy or alkylthio radical, a naphthyl radical, an indolyl radical, a quinolyl radical or a phenylamino radical in which the phenyl ring is optionally substituted by at least one substituent, said substituent being a halogen atom or an alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'-COOX, —O—alk—COOX, —CH=CH—COOX, —CO—COOX, —alk—SO$_3$H in salt form, —CH=CH—alk', —C(=NOH)-COOX, —S—alk—COOX, —SO—alk—COOX, —SO$_2$—alk—COOX, —O—CH$_2$—alk'-COOX, —CX=N-O—alk—COOX, —alk—N(OH)—CO—alk, —alk—SO$_2$H, —SO$_2$—NH—CO—R$_{11}$, —SO$_2$—NH—SO$_2$—R$_{11}$, —CO—NH—CO—R$_{11}$, —CO—NH—SO$_2$—R$_{11}$, —B(OH)$_2$, —C(NH$_2$)=NOH, —SO$_2$—NH—R$_{12}$, —CO—NH—R$_{12}$,

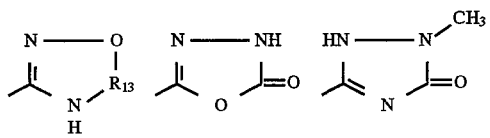

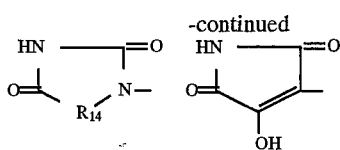

or 2,2-dimethyl-4,6-dioxo-1,3-dioxan-5-yl radical,

R$_6$ represents a hydroxyl, alkoxy, cycloalkyloxy, cycloalkylalkyloxy, phenyl or —NR$_9$R$_{10}$ radical, R"$_6$ represents an alkoxy, cycloalkyloxy, cycloalkylalkyloxy, phenyl or —NR$_9$R$_{10}$ radical, R$_7$ represents a hydrogen atom or an alkyl radical, a phenylalkyl radical or a phenyl radical optionally substituted by at least one substituent, said substituent being a halogen atom or an alkyl, alkoxy or alkylthio radical, R$_8$ represents an alkyl radical, a phenylalkyl radical or a phenyl radical optionally substituted by at least one substituent, said substituent being a halogen atom or an alkyl, alkoxy or alkylthio radical, or else R$_7$ and R$_8$ form, with the nitrogen atom to which they are attached, a saturated or unsaturated, mono- or polycyclic heterocycle containing 4 to 9 carbon atoms and at least one hetero atom, said hetero atom being O or N and optionally substituted by one or more alkyl radicals, R$_9$ represents a hydrogen atom or an alkyl radical, a cycloalkylalkyl radical, a cycloalkyl radical, a phenylalkyl radical or a phenyl radical optionally substituted by at least one substituent, said substituent being a halogen atom or an alkyl, alkoxy or alkylthio radical, R$_{10}$ represents an alkyl radical, a cycloalkylalkyl radical, a cycloalkyl radical, a phenylalkyl radical or a phenyl radical optionally substituted by at least one substituent, said substituent being a halogen atom or an alkyl, alkoxy or alkylthio radical, or R$_9$ and R$_{10}$ form, together with the nitrogen atom to which they are attached, a saturated or unsaturated, mono- or polycyclic heterocycle containing 4 to 9 carbon atoms and at least one hetero atom, said hetero atom being O, N, or S and optionally substituted by one or more alkyl radicals, R$_{11}$ represents an alkyl radical, a cycloalkyl radical, a trifluoromethyl radical or a phenyl radical optionally substituted by at least one substituent, said substituent being a cyano, alkoxy, nitro or amino radical or a halogen atom, R$_{12}$ represents a 5-tetrazolyl radical, R$_{13}$ represents C=O or S=O, R$_{14}$ represents O or C=O, n is equal to 0, 1 or 2, m is equal to 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, wherein n is other than 0 when R and R$_3$ each represent a hydrogen atom and R$_1$ represents a pyridyl radical optionally substituted by one or more alkyl radicals, a furyl radical optionally substituted by one or more alkyl radicals, a thienyl radical optionally substituted by one or more alkyl radicals, a quinolyl radical optionally

23 substituted by one or more alkyl radicals, a naphthyl radical optionally substituted by one or more alkyl radicals, an indolyl radical optionally substituted by one or more alkyl radicals or a phenyl radical optionally substituted by at least one substituent, said substituent being a halogen atom or an alkyl, alkoxy, hydroxyl, nitro, amino, monoalkylamino, dialkylamino, alkoxycarbonyl, —CO—NR$_7$R$_8$, —NH—CO—CH$_3$, trifluoromethyl or trifluoromethoxy radical, and wherein, except when otherwise mentioned, said alkyl, alkylene and alkoxy radicals and said alkyl, alkylene and alkoxy portions of radicals contain 1 to 4 carbon atoms in a straight or branched chain, said acyl radicals and portions of radicals contain 2 to 4 carbon atoms and said cycloalkyl radicals and portions of radicals contain 3 to 6 carbon atoms; a salt thereof or an isomer thereof when said salt or said isomer contains at least one asymmetric center.

2. A compound of formula (I) according to claim 1, wherein R$_1$ represents an isopropenyl, cyclohexyl, tetrahydrophenyl, cyclopentadiene, dihydrophenyl, norbornyl, adamantyl or norbornenyl radical; a salt thereof or an isomer thereof when said salt or said isomer contain at least one asymmetric center.

3. A compound of formula (I) according to claim 1, wherein R$_7$ and R$_8$ form, with the nitrogen atom to which they are attached, a hetrocycle selected from a piperidino ring optionally substituted by one or more alkyl radicals or a 1,2,3,4-tetrahydroquinoline ring-system.

4. A compound of formula (I) according to claim 1, wherein R$_9$ and R$_{10}$ form, with the nitrogen atom to which they are attached, a heterocycle, said heterocycle being a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring-system, wherein said ring systems are optionally substituted by at least one alkyl radical.

5. A compound of formula (I) according to claim 1, wherein R represents a hydrogen atom or an alkyl or phenyl radical, R$_1$ represents an alkyl or phenyl radical, R$_2$ represents a —(CH$_2$)$_n$—CO—R$_6$ chain, R$_3$ represents a hydrogen atom or an alkyl radical, R$_4$ represents an alkyl radical, R$_5$ represents a phenylamino radical in which the phenyl ring is substituted by a carboxyl radical, R$_6$ represents an alkoxy radical and n is equal to 0; a salt thereof or an isomer thereof.

6. A compound selected from:
—(S)-3-{3-[-2-(2-tert-butoxycarbonyl-5,5-diphenyl-1-pyrrolidinyl)-2-oxoethyl]ureido}benzoic acid;
—(2S,5R)-3-{3-[-2-(2-tert-butoxycarbonyl-5-methyl-5-phenyl-1-pyrrolidinyl)-2-oxoethyl]ureido}benzoic acid;
—(2RS,5SR)-3-{3-[-2-(2-tert-butoxycarbonyl-2-methyl-5-phenyl-1-pyrrolidinyl)-2-oxoethyl]ureido}benzoic acid;
—(2S,5S)-3-{3-[-2-(2-tert-butoxycarbonyl-5-butyl-1-pyrrolidinyl)-2-oxoethyl]ureido}benzoic acid; the salts of these compounds and the isomers of these compounds.

7. A process for the preparation of a compound of formula (I) as claimed in claim 1 wherein R$_5$ represents an optionally substituted phenylamino radical, which comprises the steps of reacting a derivative of carbamic acid, optionally obtained in situ by reacting a derivative of carbonic acid, said reactive derivative of carbonic acid being N,N'-carbonyldiimidazole, phosgene, diphosgene, triphosgene or p-nitrophenyl

24 chloroformate, with a derivative of formula:

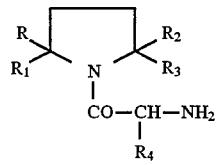

(II)

in which R, R$_1$, R$_2$, R$_3$ and R$_4$ have the same meanings as in claim 1, with an aniline in which the phenyl ring is optionally substituted by at least one substitutent, said substituent being a halogen atom or an alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —aly-O-CO—alk, —alk—COOX, —alk—O—alk, —alk'-COOX, —O—alk—COOX, —CH=CH—COOX, —CO—COOX, —alk—SO$_3$H in salt form, —CH=CH—alk', —C(=NOH)-COOX, —S—alk—COOX, —SO—alk—COOX, —SO$_2$—alk—COOX, —O—CH$_2$—alk'-COOX, —CX=N—O—alk—COOX, —alk-N( OH)-CO—alk, —alk—SO$_2$H, —SO$_2$—NH—CO—R$_{11}$, —SO$_2$—NH-SO$_2$—R$_{11}$, —CO—NH—CO—R$_{11}$, —CO—NH—SO$_2$—R$_{11}$, —B(OH)$_2$, —C(NH$_2$)=NOH, —SO$_2$—NH—R$_{12}$, —CO—NH—R$_{12}$,

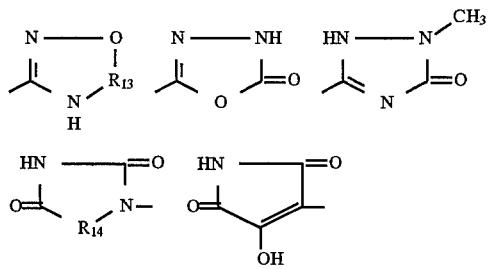

or 2,2-dimethyl-4,6-dioxo-1,3-dioxan-5-yl radical, and isolating the product of said reaction and optionally converting said isolated product to a salt.

8. A process for the preparation of a compound of formula (I) as claimed in claim 1, wherein R$_5$ represents a phenylamino radical in which the phenyl ring is optionally substituted by at least one substituent, said substituent being a halogen atom or an alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O-CO—alk, —CH=CH—alk', —alk—O—alk, trifluoromethylsulphonamido, —alk—SO$_3$H (in salt form), —O—alk—COOX, CH=CH—COOX, —CO—COOX, —S—alk—COOX, —SO—alk—COOX, —SO$_2$—alk—COOX, —O-CH$_2$—alk'-COOX, —CX=N-O—alk—COOX, —alk—COOX or —alk'-COOX radical in which X is other than a hydrogen atom, which comprises the steps of reacting a derivative of formula:

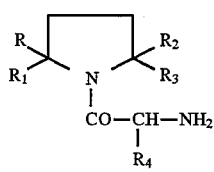

(II)

in which R, R$_1$, R$_2$, R$_3$ and R$_4$ have the same meanings as in claim 1, with a phenyl isocyanate in which the phenyl ring is optionally substituted by at least one substituent, said substituent being a halogen atom or an alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O-CO—alk, —CH=CH— alk', —alk—O—alk, trifluoromethylsulphonamido, —alk—SO$_3$H (in salt form), —O—alk—COOX, —CH=CH—COOX, —CO—COOX, —S—alk—COOX, —SO—alk—COOX, —SO$_2$—alk—COOX, —O—CH$_2$—alk'-COOX, —CX=N-O—alk—COOX, —alk—COOX or alk'-COOX radical in which X is other than a hydrogen atom, isolating the product of said reaction and optionally converting the isolated product to a salt.

9. A process for the preparation of a compound of formula (I) as claimed in claim 1, wherein R$_5$ represents a naphthyl, indolyl, quinolyl or optionally substituted phenyl radical, which comprises the steps of reacting a derivative of formula:

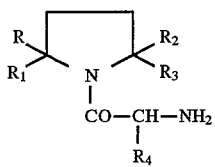
(II)

in which R, R$_1$, R$_2$, R$_3$ and R$_4$ have the same meanings as in claim 1, with an acid of formula HOOC-R$_5$ in which R$_5$ has the same meaning as above, or a derivative of this acid, isolating the product of said reaction and optionally converting the isolated product to a salt.

10. A process for the preparation of a compound of formula (I) as claimed in claim 1, wherein R$_5$ represents a phenylamino radical in which the phenyl ring is substituted by a carboxyl, —alk—COOH, —O—alk—COOH, —alk'-COOH, —CH=CH—COOH, —CH—COOH, —S—alk—COOH, —SO—alk—COOH, —SO$_2$—alk—COOH, —C(=NOH)-COOH, —O—CH$_2$—alk'-COOH or —CX=N-O—alk—COOH radical and/or R$_2$ represents a —(CH$_2$)$_n$—COOH chain, which comprises the steps of hydrolysing a corresponding ester of formula (I) or subjecting a corresponding ester of formula (I) to hydrogenolysis, isolating the product of said hydrolysing or hydrogenolysis step and optionally converting said isolated product to a salt.

11. A process for the preparation of a compound of formula (I) as claimed in claim 1, wherein R$_5$ represents a phenylamino radical in which the phenyl ring is substituted by a hydroxyiminoalkyl or alkoxyiminoalkyl radical, which comprises the steps of reacting a corresponding acylated derivative of formula (I) with a derivative of formula:

H$_2$N—OR$_{18}$ (XIV)

in which R$_{18}$ represents a hydrogen atom or an alkyl radical, isolating the product of said reaction and optionally converting said isolated product to a salt.

12. A process for the preparation of a compound of formula (I) as claimed in claim 1, wherein R$_2$ represents a —(CH$_2$)$_n$—CO-R$_6$ chain, R$_6$ not being a hydroxyl radical, and R$_5$ represents a naphthyl indolyl, quinolyl or optionally substituted phenyl radical or a phenylamino radical in which the phenyl ring is optionally substituted by at least one substituent, said substituent being a halogen atom or an alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O-CO—alk, —CH=CH— alk', —alk—O—alk, trifluoromethylsulphonamido, —alk—SO$_3$H (in salt form), —O—alk—COOX, —CH=CH—COOX, —CO—COOX, —S—alk—COOX, —SO—alk—COOX, SO$_2$—alk—COOX, —O—CH$_2$—alk'-COOX, —CX=N-O—alk—COOX, —alk—COOX or—alk'-COOX radical in which X is other than a hydrogen atom, which comprises the steps of reacting a derivative of formula:

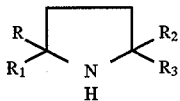
(IV)

in which R, R$_1$ and R$_3$ have the same meanings as in claim 1 and R$_2$ has the same meaning as above, with an acid of:

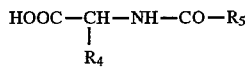
(XV)

in which R$_5$ has the same meaning as above, or a reactive derivative of this acid, and R$_4$ has the same meaning as in claim 1, isolating the product of said reaction and optionally converting said isolated product to a salt.

13. A pharmaceutical composition comprising a pharmaceutically effective amount of a compound of formula (I) according to claim 1 and a pharmaceutically acceptable carrier.

14. A method of treating disorders linked to cholecystokinin and gastrin, which comprises administering to a host in need of said treatment an effective amount of a compound of formula (I) according to claim 1.

* * * * *

UNITED STATES PATENT AND TRADEMARK OFFICE
CERTIFICATE OF CORRECTION

PATENT NO. : 5,624,939
DATED : April 29, 1997
INVENTOR(S) : Marc CAPET et al.

It is certified that error appears in the above-indentified patent and that said Letters Patent is hereby corrected as shown below:

Claim 3, column 23, line 27, "hetrocycle" should read --heterocycle--.

Claim 3, column 23, line 29, "1,2.3,4-tetrahydroquinoline" should read --1,2,3,4-tetrahydroquinoline--.

Claim 7, column 24, line 11, "substitutent" should read --substituent--.

Signed and Sealed this

Eighteenth Day of August, 1998

Attest:

BRUCE LEHMAN

*Attesting Officer*

*Commissioner of Patents and Trademarks*

UNITED STATES PATENT AND TRADEMARK OFFICE
CERTIFICATE OF CORRECTION

PATENT NO. : 5,624,939
DATED : April 29, 1997
INVENTOR(S) : Marc CAPET et al.

It is certified that error appears in the above-identified patent and that said Letters Patent is hereby corrected as shown below:

Claim 3, column 23, line 27, "hetrocycle" should read --heterocycle--.

Claim 3, column 23, line 29, "1,2.3,4-tetrahydroquinoline" should read --1,2,3,4-tetrahydroquinoline--.

Claim 7, column 24, line 11, "substitutent" should read --substituent--.

Signed and Sealed this

Twenty-second Day of September, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,624,939
DATED : April 29, 1997
INVENTOR(S) : Marc CAPET et al.

It is certified that error appears in the above-indentified patent and that said Letters Patent is hereby corrected as shown below:

Claim 1, colum 21, line 50, "—alk'-COOX." should read ---alk'-COOX,--.

Signed and Sealed this

Eighth Day of June, 1999

Attest:

Q. TODD DICKINSON

Attesting Officer     Acting Commissioner of Patents and Trademarks